United States Patent [19]

Boigegrain et al.

[11] Patent Number: 5,561,234
[45] Date of Patent: Oct. 1, 1996

[54] 1-(7-CHLOROQUINOLIN-4-YL)PYRAZOLE-3-CARBOXAMIDE N-OXIDE DERIVATIVES, METHOD OF PREPARING THEM, AND THEIR PHARMACEUTICAL COMPOSITIONS

[75] Inventors: Robert Boigegrain, Assas; Danièle Gully, Saubens; Francis JeanJean, Valflaunes; Antoine Pradines, Roquettes, all of France

[73] Assignee: Sanofi, Paris, France

[21] Appl. No.: 499,726

[22] Filed: Jul. 7, 1995

[30] Foreign Application Priority Data

Jul. 8, 1994 [FR] France .................. 94 08459

[51] Int. Cl.$^6$ .................. C07D 401/04; A61K 31/47
[52] U.S. Cl. .................. 546/167
[58] Field of Search .................. 546/167; 514/314

*Primary Examiner*—David B. Springer
*Attorney, Agent, or Firm*—Bacon & Thomas

[57] ABSTRACT

The present invention relates to compounds of the formula

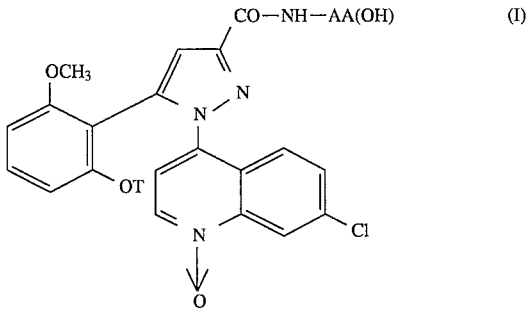

in which
T is hydrogen, a $C_1$–$C_4$-alkyl, a $C_3$–$C_8$-cycloalkyl, a $C_3$–$C_8$-cycloalkylmethyl or a methoxyethyl; and
the group —NH—AA(OH) is the amino acid residue of the formula

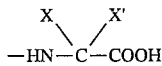

where X is hydrogen, a $C_1$–$C_5$-alkyl or a $C_3$–$C_{15}$ non-aromatic carbocyclic radical and X' is hydrogen, or alternatively X and X', together with the carbon atom to which they are bonded, form a $C_3$–$C_{15}$ non-aromatic carbocycle, and salts thereof.

11 Claims, No Drawings

1-(7-CHLOROQUINOLIN-4-YL)PYRAZOLE-3-CARBOXAMIDE N-OXIDE DERIVATIVES, METHOD OF PREPARING THEM, AND THEIR PHARMACEUTICAL COMPOSITIONS

The present invention relates to novel substituted 1-(7-chloroquinolin-4-yl)pyrazole-3-carboxamide N-oxides with a high affinity for the neurotensin receptor, to a method of preparing them and to pharmaceutical compositions in which they are present as active principles.

The first potential synthetic non-peptide drugs capable of binding to the neurotensin receptors were described in EP-0477049. Said drugs are pyrazole-3-carboxamides variously substituted by amino acids, which, at submicromolar doses, displace iodinated neurotensin from its receptor on human brain membranes. This series led to the development of the compound 2-{[1-(7-chloroquinolin-4-yl)-5-(2,6-dimethoxxphenyl)pyrazol-3-yl]carbonylamino}adamantane-2-carboxylic acid, hereafter called SR48692, which possesses a potent and selective activity as a neurotensin antagonist (D. Gully et al., Proc. Natl. Acad. Sci. USA, 1993, 90, 65–69).

The characteristic of the series of products described in EP-0477049 is the presence particularly of a substituted or unsubstituted phenyl, naphthyl or quinolin-4-yl group in the 1-position of the pyrazole ring. More particularly, SR48692 has a 7-chloroquinolin-4-yl group in the 1-position of the pyrazole.

It has now been found that by oxidizing the nitrogen of the 7-chloroquinolin-4-yl group of pyrazole-3-carboxamide derivatives under mild conditions, molecules are obtained which, compared with their precursors not oxidized on the nitrogen, have at least the same activity towards the neurotensin receptors and also have a better solubility, particularly in water.

Thus these novel compounds according to the invention are particularly valuable in that they enable injectable solutions to be prepared.

Moreover, they are compatible with numerous galenic formulations for oral administration because they have a better bioavailability.

According to one of its features, the present invention therefore relates to substituted 1-(7-chloroquinolin-4-yl)pyrazole-3-carboxamide N-oxides of the formula

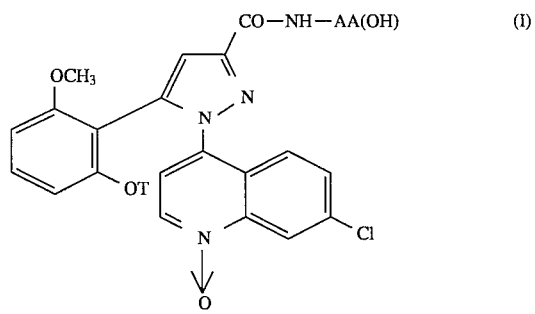 (I)

in which

T is hydrogen, a $C_1$–$C_4$-alkyl, a $C_3$–$C_8$-cycloalkyl, a $C_3$–$C_8$-cycloalkylmethyl or a methoxyethyl; and the group —NH—AA(OH) is the amino acid residue

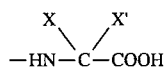

where X is hydrogen, a $C_1$–$C_5$-alkyl or a $C_3$–$C_{15}$ non-aromatic carbocyclic radical and X' is hydrogen, or alternatively X and X', together with the carbon atom to which they are bonded, form a $C_3$–$C_{15}$ non-aromatic carbocycle, and salts thereof.

$C_1$–$C_4$-alkyl or $C_1$–$C_5$-alkyl is understood as meaning a linear or branched alkyl.

The $C_3$–$C_{15}$ non-aromatic carbocyclic radicals include saturated or unsaturated, fused or bridged monocyclic or polycyclic radicals, which may be terpene radicals. These radicals are optionally monosubstituted or polysubstituted by a $C_1$–$C_4$-alkyl.

The monocyclic radicals include $C_3$–$C_{12}$-cycloalkyls, for example cyclopropyl, cyclopentyl, cyclohexyl, cycloheptyl, cyclooctyl and cyclododecyl.

In the above amino acid residue, if X and X', together with the carbon atom to which they are bonded, form a $C_3$–$C_{15}$ non-aromatic carbocycle, said carbocycle is as defined for the corresponding radicals above.

Adamantane is the preferred non-aromatic polycyclic carbocycle. Thus, if X' is hydrogen, X is a 1-adamantyl or 2-adamantyl group, and if —C(XX') together form a carbocycle, this radical is the 2-adamantylidene radical.

Cyclopentane and cyclohexane are particularly preferred among the non-aromatic carbocycles.

The preferred substituted quinolinylpyrazole N-oxides according to the present invention are those of formula (I) in which:

T is a methyl or cyclopropylmethyl group and the Group —NH—AA(OH) is the 2-aminoadamantane-2-carboxylic acid or (S)-2-amino-2-cyclohexylacetic acid residue, and salts thereof.

The salts are those with alkali metals, preferably sodium or potassium, alkaline earth metals, preferably calcium, and organic bases such as diethylamine, tromethamine, meglumine (N-methyl-D-glucamine), lysine, arginine, histidine or diethanolamine.

The salts of the compounds of formula I according to the present invention also include those with mineral or organic acids which permit a suitable separation or crystallization of the compounds of formula I, such as picric acid, oxalic acid or an optically active acid, for example a mandelic acid or a camphosulfonic acid, and mineral or organic acids which form pharmaceutically acceptable salts such as the hydrochloride, hydrogensulfate, dihydrogenphosphate, methanesulfonate, maleate, fumarate, 2-naphthalene-2-sulfonate or isethionate.

If the compounds (I) include an asymmetric carbon, the enantiomers form part of the invention.

If the group —NH(AA)OH is a cycloaliphatic amino acid residue, the compounds of formula (I) include both those in which the amine group is in the endo position relative to the aliphatic cyclic system, and those in which the amine group is in the exo position relative to the aliphatic cyclic system.

According to another feature, the present invention relates to a method of preparing the substituted 1-(7-chloroquinolin-4-yl)pyrazole-3-carboxamide N-oxides of formula (I) and salts thereof with mineral or organic bases, which comprises treating a derivative of the formula

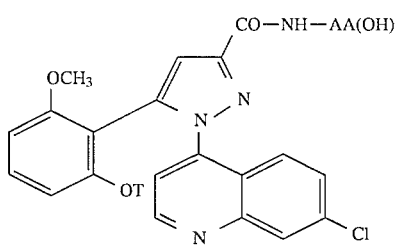

in which T and AA (OH) are as defined above for the compound of formula (T), with an oxidizing agent at room temperature in an aprotic solvent to give the compounds (I) or a salt thereof.

The oxidizing agents used are well known to those skilled in the art and are selected for example from:

magnesium monoperoxyphthalate hexahydrate (or MPPH)

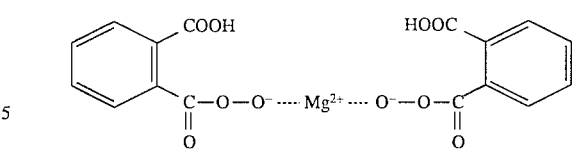

perbenzoic acid
metachloroperbenzoic acid (or mCPBA)
perphthalic acid
performic acid
peracetic acid.
Other peracids can also be used.

The solvents used are those conventionally used by those skilled in the art for oxidation reactions, for example dipolar aprotic solvents such as dimethylformamide, or chlorinated solvents such as dichloromethane or chloroform.

A preferred oxidizing agent is metachloroperbenzoic acid, which produces good yields under mild oxidation conditions. The reaction temperature is preferably room temperature, making it possible to avoid the formation of degradation or hydroxylation products.

According to EP-0477049, the compounds of formula (II) are prepared by SCHEME 1 below:

SCHEME 1

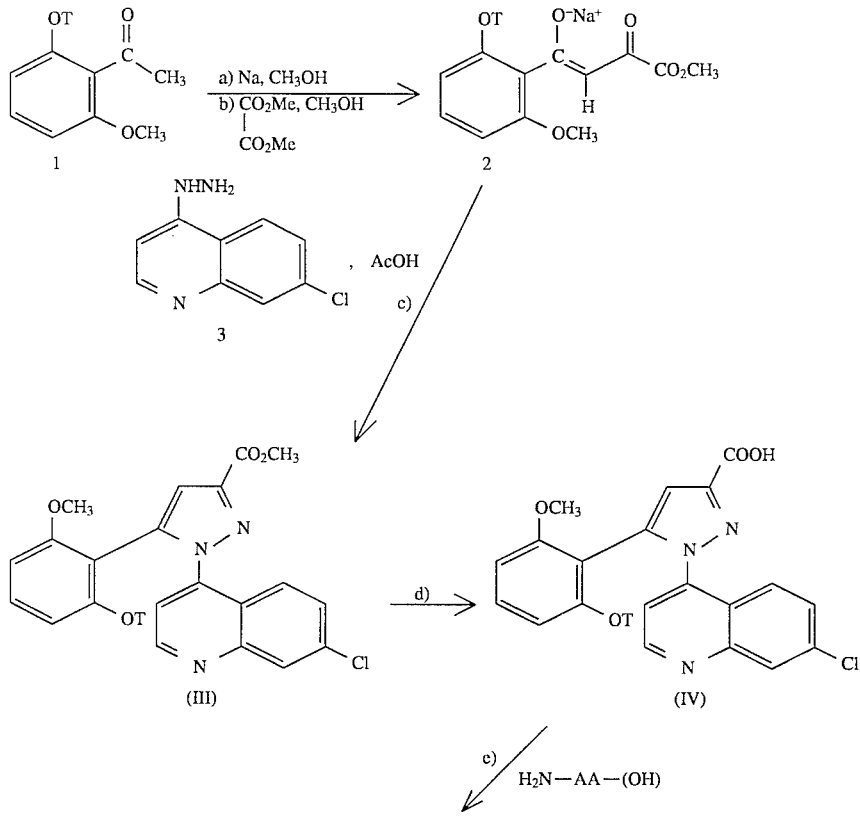

-continued
SCHEME 1

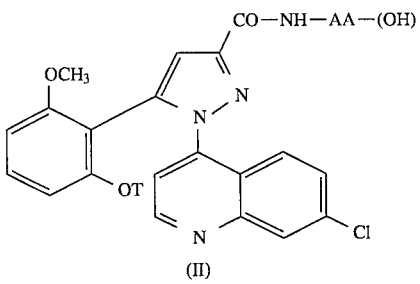

(II)

In the first step, a), a strong base such as sodium methylate is reacted with a ketone of formula 1, in which T is as defined above, this being followed (step b)) by reaction with an equimolar amount of methyl oxalate in an alkanol, for example methanol, according to L. Claisen, Ber., 1909, 42, 59. After precipitation in an ether such as diethyl ether or diisopropyl ether, the sodium enolates 2 are filtered off. It is also possible to prepare a lithium enolate according to W. V. Murray et al., *J. Heterocyclic Chem.*, 1989, 26, 1389.

The metal enolate 2 prepared in this way, and an excess of 7-chloro-4-(hydrazin-1-yl)quinoline derivative 3 or a salt thereof, are then refluxed in acetic acid (step c)) to give the esters (III).

Saponification of the esters (III) by reaction with an alkaline agent, for example potassium hydroxide or sodium hydroxide, followed by acidification, gives the acids (IV) (step d).

As a functional derivative of the substituted 7-chloroquinolin-4-ylpyrazole-3-carboxylic acid of formula (IV), it is possible to use the acid chloride, the anhydride, a mixed anhydride, a $C_1$–$C_4$-alkyl ester, an activated ester, for example the p-nitrophenyl ester, or the free acid appropriately activated with, for example, N,N-dicyclohexylcarbodiimide or benzotriazol-N-oxytris(dimethylamino)phosphonium hexafluorophosphate (BOP).

The amino acids of the formula $NH_2$—AA—(OH) can be used either as such or after prior protection with protecting groups conventionally used in peptide synthesis.

Thus, in step e) of the method, the chloride of a 1-(7-chloroquinolin-4-yl)pyrazole-3-carboxylic acid, obtained by reacting thionyl chloride with an acid of formula (IV), can be reacted with an amino acid in a solvent such as acetonitrile, THF, DMF or dichloromethane, under an inert atmosphere, at room temperature, for a period of between a few hours and a few days, in the presence of a base such as pyridine, sodium hydroxide or triethylamine.

One variant of step e) consists in preparing the acid chloride or the mixed anhydride of a 7-chloroquinolin-4-ylpyrazole-3-carboxylic acid by reacting isobutyl or ethyl chloroformate with an acid of formula (IV), and in reacting it with an N,O-bistrimethylsilyl derivative of an amino acid, obtained by an adaptation of the method described in the publication by M. T. Nagasawa et al., *J. Med. Chem.*, 1975, 18, 8, 826–830, by reacting bis(trimethylsilyl)acetamide, 1,3-bis(tri-methylsilyl)urea or bis(trifluoromethyl)acetamide with an amino acid of the formula $NH_2$—AA—(OH) in solvents such as acetonitrile or dichloromethane, under an inert atmosphere, at room temperature, or at the reflux temperature of the solvent, for a period of between a few hours and one day.

Another variant of the procedure of step e) consists in reacting the mixed anhydride of a pyrazole-3-carboxylic acid with an amino acid of the formula $NH_2$—AA—(OH) in a solvent such as dichloromethane, under an inert atmosphere, at room temperature, for a period of between one day and a few days, in the presence of a base such as triethylamine.

The 7-chloroquinolin-4-ylpyrazole-3-carboxylic acids of formula (IV):

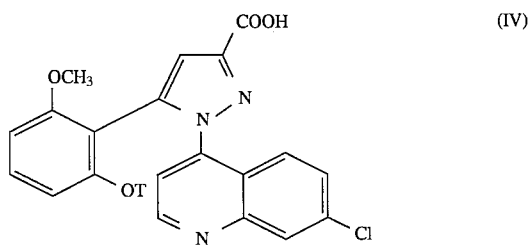

in which T is a $C_3$–$C_8$-cycloalkyl, a $C_3$–$C_8$-cycloalkylmethyl or a methoxyethyl, and the functional derivatives of the acid group, are novel and, as key intermediates in the preparation of the compounds (I), constitute a further feature of the present invention.

The compounds of formula (II):

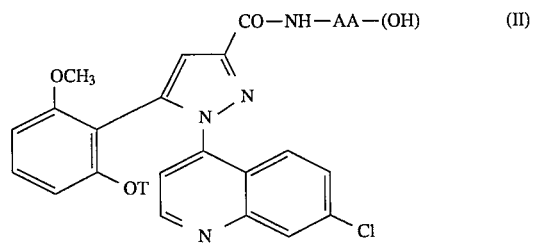

in which T is a $C_3$–$C_8$-cycloalkyl, a $C_3$–$C_8$-cycloalkylmethyl or a methoxyethyl are also novel and constitute a further feature of the invention.

If the product of formula (II) is obtained in the acid form, it can be converted to a metal salt, especially an alkali metal salt such as the sodium salt, or an alkaline earth metal salt such as the calcium salt, by the conventional methods.

The amino acids not available commercially are prepared by the synthesis of Strecker, Ann., 1850, 75, 27, or by the synthesis of H. T. Bucherer et al., *J. Pract. Chem.*, 1934, 141, 5, followed by hydrolysis to give the amino acids; for example, 2-aminoadamantane-2-carboxylic acid is prepared according to H. T. Nagasawa et al., *J. Med. Chem.*, 1973, 16, (7), 823, or according to M. Paventi et al., Can. J. Chem., 1987, 65, 2114.

α-Amino-1-adamantylacetic and α-amino-2-adamantylacetic acids are prepared according to B. Gaspert et al., *Croatico Chemica Acta*, 1976, 48, (2), 169–178.

2-Aminonorbornane-2-carboxylic acid is prepared according to H. S. Tager et al., *J. Am. Chem. Soc.*, 1972, 94, 968.

The α-aminocycloalkylcarboxylic acids are prepared according to J. W. Tsang et al., *J. Med. Chem.,* 1984, 27, 1663.

The R- and S-cyclopentylglycines are prepared according to European patent application EP-477049.

The R- and S-cyclohexylglycines are prepared according to Rudman et al., *J. Am. Chem. Soc.,* 1952, 74, 551.

The R- and S-cyclohexylglycines can also be prepared by catalytic hydrogenation of the R- and S-phenylglycines.

The α-aminocycloalkylcarboxylic acids of R or S configuration can also be prepared by stereospecific enzymatic hydrolysis of the corresponding racemic N-acetyl derivatives according to J. Hill et al., *J. Org. Chem.,* 1965, 1321.

The compounds of formula (I) above also include those in which one or more hydrogen or carbon atoms have been replaced with their radioactive isotope, for example tritium or carbon-14. Such labeled compounds are useful in research, metabolic or pharmacokinetic studies and in biochemical assays as receptor ligands.

The compounds of formula (I) and salts thereof with mineral or organic bases possess a very great affinity for the human neurotensin receptors in the tests described in the publication by D. Gully et al. cited above. More particularly, compared with the 1-naphthyl and 4-chloro-1-naphthyl derivatives described in EP-0477049, which have an $IC_{50}$ equal to or greater than 100 nM, the compounds of the invention have a markedly lower $IC_{50}$ ranging from a few nM to 50 nM. Of particular interest are the products of formula (I) in which T is methyl or cyclopropylmethyl, especially the amide with 2-aminoadamantane-2-carboxylic acid, which have an $IC_{50}$ of the order of 2 nM.

This compound is therefore even more active than SR48692, which is unexpected in view of the already very high activity of the compounds described in EP-0477049.

Furthermore, the N-oxide compounds, in particular the one described in EXAMPLE 2 below, namely 2-{[1-(1-oxido-7-chloroquinolin-4-yl)-5-(2,6-dimethoxyphenyl)pyrazol-3-yl]carbonylamino}adamantane-2-carboxylic acid, were subjected to a comparative solubility study with SR48692.

The media studied are water, ethanol and a water/polyethylene glycol 400 mixture (70/30 v/v).

The solubility measurements were made at 25° C. after stirring of the saturated solutions for 3 or 5 hours.

After achieving conditions under which the products solubilized in water are not adsorbed on certain filters, the solutions are filtered and then assayed by liquid chromatography (column μmBondapak C18, eluent acetonitrile/trifluoroacetic acid, detection at 254 nm, flow rate 1 ml/minute).

The following results are obtained:

TABLE I

Comparative solubility study of SR48692 and the compound of EXAMPLE 2

|  | SR48692 | COMPOUND OF EXAMPLE 2 |
| --- | --- | --- |
| water | 0.4 μg/ml | 1.7 μg/ml |
| ethanol | 1.3 mg/ml | 10.3 mg/ml |
| water/PEG | less than 1 μg/ml | 30 μg/ml |

This study shows the unexpected higher solubility of the compound of EXAMPLE 2, particularly in water and the water/polyethylene glycol mixture, which are suitable solvents for the preparation of injectable forms. By way of a complementary example, the solubility of the compounds in ethanol has been indicated.

The compounds of the present invention have a low toxicity; in particular, their acute toxicity is compatible with their use as drugs. For such a use, an effective amount of a compound of formula (I) or a pharmaceutically acceptable salt thereof is administered to mammals for the treatment of pathological conditions associated with a dysfunction of the dopaminergic systems, for example as antipsychotics [D. R. Handrich et al., Brain Research, 1982, 231, 216–221, and C. B. Nemeroff, Biological Psychiatry, 1980, 15, (2), 283–302], or in disorders of the cardiovascular or gastrointestinal systems.

Thus, according to another feature, the present invention relates to pharmaceutical compositions in which the compounds of formula (I) or pharmaceutically acceptable salts thereof, where appropriate, are present as active principles.

In the pharmaceutical compositions of the present invention for oral, sublingual, subcutaneous, intramuscular, intravenous, transdermal or rectal administration, the active principles can be administered to animals and humans in unit forms of administration, or as a mixture with conventional pharmaceutical carriers. The appropriate unit forms of administration include forms for oral administration, such as tablets, gelatin capsules, powders, granules and oral solutions or suspensions, forms for sublingual and buccal administration, forms for subcutaneous, intramuscular or intravenous administration and forms for rectal administration.

To obtain the desired effect, the dose of active principle can vary between 0.5 and 1000 mg per day, preferably between 2 and 500 mg.

Each unit dose can contain from 0.5 to 250 mg of active principle, preferably from 1 to 125 mg, in combination with a pharmaceutically acceptable vehicle. This unit dose can be administered 1 to 4 times a day.

If a solid composition is prepared in the form of tablets, the active principle is mixed with a pharmaceutically acceptable vehicle such as gelatin, starch, lactose, magnesium stearate, talc, gum arabic or the like. The tablets can be coated with sucrose or other appropriate substances or else they can be treated so as to have a sustained or delayed activity and so as to release a predetermined amount of active principle continuously.

A gelatin capsule preparation is obtained by mixing the active principle with a diluent and pouring the resulting mixture into soft or hard gelatin capsules.

A preparation in the form of a syrup or elixir can contain the active principle together with a sweetener, which is preferably calorie-free, methylparaben and propylparaben as antiseptics, a flavoring and an appropriate color.

The water-dispersible powders or granules can contain the active principle mixed with dispersants, wetting agents or suspending agents such as polyvinylpyrrolidone and the like, as well as with sweeteners or taste correctors.

The active principle can also be presented in the form of a complex with a cyclodextrin, for example α-, β- or γ-dextrin, 2-hydroxypropyl-β-cyclodextrin or methyl-β-cyclodextrin.

Rectal administration is effected using suppositories which are prepared with binders melting at the rectal temperature, for example cocoa butter or polyethylene glycols.

The active principle can also be formulated as microcapsules, optionally with one or more carriers.

The following Examples, which are given without implying a limitation, illustrate the invention. The methods of synthesizing the different intermediates for obtaining the compounds of the invention are described in the PREPARATIONS below.

The melting points were measured on a Koffler heating bench.

The compounds according to the invention give the theoretical percentage analyses.

The nuclear magnetic resonance spectra and mass spectra are also consistent with the structure of the compounds described in the EXAMPLES below.

PREPARATION I 5 g of 2-hydroxy-6-methoxyacetophenone are dissolved in 100 ml of isopropanol in the presence of 1.2 equivalents (6.3 ml) of cesium hydroxide as a 50% solution in water. The mixture is stirred for ten minutes and then concentrated under vacuum, taken up with isopropanol and concentrated under vacuum. The residue is taken up with 30 ml of dimethylformamide, a solution of 1.2 equivalents (3.5 ml) of cyclopropylmethyl bromide is then added and the reaction mixture is heated at 80° C. for 4 hours. It is concentrated under vacuum, the residue is taken up with ethyl acetate and washed successively with a saturated solution of NaCl and with water, and the organic phase is decanted, dried and concentrated under vacuum to give 5.1 g of the expected 2-cyclopropylmethoxy-6-methoxyacetophenone.

PREPARATION II 0.53 g of sodium is dissolved in 15 ml of methanol, and a solution of 5.1 g of the compound prepared above and 1 equivalent (3.4 g) of dimethyl oxalate in 25 ml of methanol is then added. The reaction mixture is refluxed for 6 hours and then cooled. Isopropyl ether is added until precipitation occurs, and the precipitate is filtered off to give 5.3 g of the expected sodium salt of the methyl ester of 4-(2-cyclopropylmethoxy-6-methoxyphenyl)-2,4-dioxobutanoic acid.

PREPARATION III 1 g of the sodium salt prepared above and 1.1 equivalents (0.65 g) of 7-chloro-4-(hydrazin-1-yl)-quinoline are suspended in 10 ml of acetic acid. The reaction mixture is heated at 100° C. for 5 hours and then poured into 150 ml of iced water and the precipitate is filtered off to give 0.74 g of the expected methyl ester of 5-(2-cyclopropylmethoxy-6-methoxyphenyl)-1-(7-chloroquinolin-4-yl)pyrazole-3-carboxylic acid.

PREPARATION IV 2.7 g of the ester prepared above are dissolved in a mixture of 25 ml of methanol and 25 ml of water in the presence of 2.5 equivalents (0.815 g) of potassium hydroxide. The reaction mixture is refluxed for two hours and then poured into iced water. Extraction is carried out with diethyl ether, the ether phase is then acidified with a solution of hydrochloric acid (pH=2) and the precipitate is filtered off and rinsed with water to give 2.5 g of the expected 5-(2-cyclopropylmethoxy-6-methoxyphenyl)-1-(7-chloroquinolin-4-yl)pyrazole-3-carboxylic acid.

PREPARATION V 2.1 equivalents (42.7 g) of bistrimethylsilylacetamide are added at room temperature to 39 g of 2-aminoadamantane-2-carboxylic acid in 680 ml of acetonitrile and the reaction mixture is then refluxed for two hours. The solution becomes clear and contains N,O-bistrimethylsilyl-2-aminoadamantane-2-carboxylic acid.

PREPARATION VI 1.35 g of the pyrazolecarboxylic acid obtained according to PREPARATION IV are dissolved in 30 ml of toluene in the presence of 2.25 ml of thionyl chloride. The reaction mixture is refluxed for 5 hours and then concentrated under vacuum. The resulting acid chloride is added to a solution obtained according to PREPARATION V and containing the equivalent of 0.59 mg of the adamantanecarboxylic acid. This reaction mixture is then refluxed for 3 hours, after which the solvent is concentrated under vacuum. The residue is taken up with a mixture of 12 ml of methanol and 2 ml of water and then stirred for 1 hour at room temperature, during which time the expected product precipitates. The precipitation at the end of hydrolysis is completed by the addition of 10 ml of water. The mixture is stirred for half an hour and the precipitate is then filtered off and washed successively with water, with pentane and then with diethyl ether to give 1.8 g of 2-{[1-(7-chloroquinolin-4-yl)-5-(2-cyclopropylmethoxy-6-methoxyphenyl)pyrazol-3-yl]carbonyl}adamantane-2-carboxylic acid after drying; m.p.= 200° C.

EXAMPLE 1

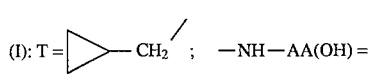 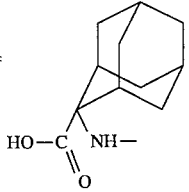

0.626 g Of the acid obtained in PREPARATION VI is dissolved in 100 ml of chloroform in the presence of 0.294 mg of metachloroperbenzoic acid and the mixture is stirred for 24 hours at room temperature. The reaction mixture is concentrated under vacuum and then taken up with 10 ml of dichloromethane. The precipitate obtained is filtered off and then washed with dichloromethane to give 0.24 g of 2-{[1-(1-oxido-7-chloroquinolin-4-yl)-5-(2-cyclopropylmethoxy-6-methoxyphenyl)pyrazol-3-yl]carbonylamino}adamantane-2-carboxylic acid; m.p.=190° C.

EXAMPLE 2

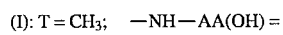 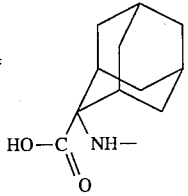

2-{[1-(7-Chloroquinolin-4-yl)-5-(2,6-dimethoxyphenyl)pyrazol-3-yl]carbonylamino}adamantane-2-carboxylic acid (SR48692) is prepared by following the procedures described in Preparations I to VI above using methyl bromide in place of the cyclopropylmethyl bromide. 0.5 g of this acid is dissolved in 80 ml of dimethylformamide, and 4.15 g of magnesium monoperoxyphthalate hexahydrate are then added. The reaction mixture is stirred and left to stand at room temperature for 24 hours. 250 ml of a 10/00 aqueous solution of trifluoro acetic acid are then added and extraction is carried out successively with 150 ml, then 100 ml and then 50 ml of dichloromethane. The extracted fractions are combined and washed twice with 250 ml of distilled water. The extract obtained after washing is concentrated under vacuum at 40° C. and the residue is then purified by preparative HPLC on a silica phase. This is done by taking up the residue with 4.5 ml of an eluent consisting of a 97/3 (v/v) dichloromethane/iso propanol mixture and eluting it on a Kromasil 100 Å–10µ phase under 40 bar. The fractions are collected every 0.2 minute, each fraction having a volume of 25 ml. Concentration of the pure product fractions gives 0.080 g of white crystals, which are washed with dichloromethane to finally give 0.050 g of 2-{[1-(1-oxido-7-chloroquinolin-4-yl)-5-(2,6-dimethoxyphenyl)-pyrazol-3-yl]carbonylamino}adamantane-2-carboxylic acid; m.p.= 205° C.

What is claimed is:

1. A compound of the formula

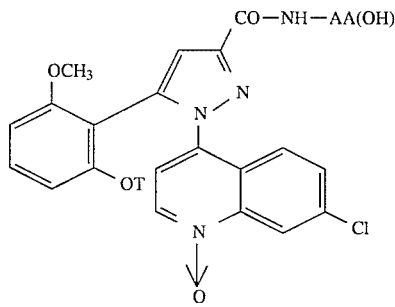

in which

T is hydrogen, a $C_1$–$C_4$-alkyl, a $C_3$–$C_8$-cycloalkyl, a $C_3$–$C_8$-cycloalkylmethyl or a methoxyethyl; and the group —NH—AA(OH) is the amino acid residue of the formula

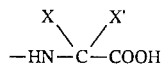

where X is hydrogen, a $C_1$–$C_5$-alkyl or a $C_3$–$C_{15}$ non-aromatic carbocyclic radical and X' is hydrogen, or alternatively X and X', together with the carbon atom to which they are bonded, form a $C_3$–$C_{15}$ non-aromatic carbocycle, and pharmaceutically acceptable salts thereof.

2. A compound according to claim 1 in which T is a methyl or cyclopropylmethyl group and the group —NH—AA(OH) is the 2-aminoadamantane-2-carboxylic acid residue, and pharmaceutically acceptable salts thereof.

3. An acid of the formula

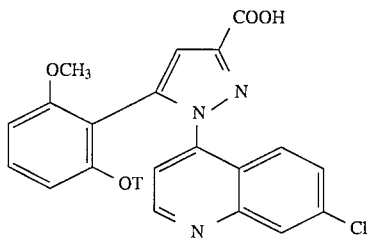

in which T is a $C_3$–$C_8$-cycloalkyl, a $C_3$–$C_8$-cycloalkylmethyl or a methoxyethyl.

4. A pharmaceutical composition in which a compound according to claim 1 or a pharmaceutically acceptable salt thereof is present as the active principle, together with a pharmaceutically acceptable carrier.

5. A pharmaceutical composition in which a compound according to claim 2 or a pharmaceutically acceptable salt thereof is present as the active principle, together with a pharmaceutically acceptable carrier.

6. A pharmaceutical composition according to claim 4 in the form of a dosage unit.

7. A pharmaceutical composition according to claim 5 in the form of a dosage unit.

8. A pharmaceutical composition according to claim 6 which contains from 0.5 to 250 mg of active principle.

9. A pharmaceutical composition according to claim 7 which contains from 0.5 to 250 mg of active principle.

10. A method of preparing the compounds of formula (I) according to claim 1 and pharmaceutically acceptable salts thereof, which comprises treating a derivative of formula

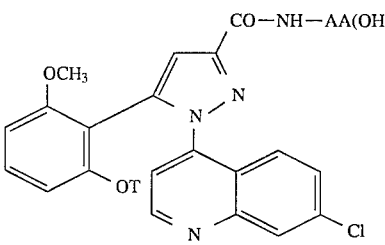

in which T and —NH—AA(OH) are as defined in claim 1 for the compound of formula (I), with an oxidizing agent selected from the group consisting of magnesium monoperoxyphthalate hexahydrate; perbenzoic acid; metachloroperbenzoic acid (or mCPBA); perphthalic acid; performic acid; and peracetic acid at room temperature in an aprotic solvent to give the compounds (I) and optionally converting the so obtained compounds (I) into their pharmaceutically acceptable salts.

11. An amide of formula

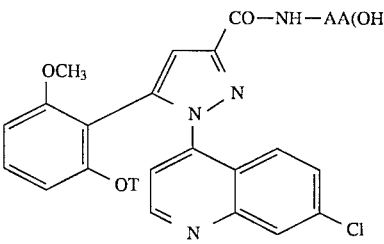

in which T is a $C_3$–$C_8$-cycloalkyl, a $C_3$–$C_8$-cycloalkylmethyl or a methoxyethyl and NH—AA(OH) is the amino acid residue of formula

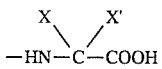

where X is hydrogen, a $C_1$–$C_5$-alkyl or a $C_3$–$C_{15}$ non-aromatic carbocyclic radical and X' is hydrogen, or alternative X and X', together with the carbon atom to which they are bonded, form a $C_3$–$C_{15}$ non-aromatic carbocycle and pharmaceutically acceptable salts thereof.

* * * * *